United States Patent
Netsu et al.

(10) Patent No.: US 9,006,002 B2
(45) Date of Patent: Apr. 14, 2015

(54) POLYCRYSTALLINE SILICON ROD AND METHOD FOR MANUFACTURING POLYCRYSTALLINE SILICON ROD

(75) Inventors: Shigeyoshi Netsu, Niigata (JP); Fumitaka Kume, Niigata (JP); Junichi Okada, Niigata (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 290 days.

(21) Appl. No.: 13/808,404

(22) PCT Filed: Jul. 4, 2011

(86) PCT No.: PCT/JP2011/003800
§ 371 (c)(1),
(2), (4) Date: Jan. 4, 2013

(87) PCT Pub. No.: WO2012/004968
PCT Pub. Date: Jan. 12, 2012

(65) Prior Publication Data
US 2013/0102092 A1  Apr. 25, 2013

(30) Foreign Application Priority Data
Jul. 6, 2010 (JP) ................. 2010-153828

(51) Int. Cl.
*H01L 21/00* (2006.01)
*H01L 21/66* (2006.01)
(Continued)

(52) U.S. Cl.
CPC .......... *H01L 22/12* (2013.01); *C01B 33/035* (2013.01); *G01N 29/045* (2013.01);
(Continued)

(58) Field of Classification Search
USPC .................................. 438/4, 14–18
See application file for complete search history.

(56) References Cited

U.S. PATENT DOCUMENTS

| 7,694,568 B2 * | 4/2010 | Hegen et al. ............ 73/627 |
| 2005/0028594 A1 * | 2/2005 | Chen et al. ............. 73/627 |
| 2008/0053232 A1 | 3/2008 | Hegen et al. |

FOREIGN PATENT DOCUMENTS

| CN | 101135673 A | 3/2008 |
| JP | 2001 21543 | 1/2001 |

(Continued)

OTHER PUBLICATIONS

Combined Chinese Office Action and Search Report issued Jun. 4, 2014 in Patent Application No. 201180033481.0 (with English translation of categories of cited documents).

(Continued)

*Primary Examiner* — Karen Kusumakar
(74) *Attorney, Agent, or Firm* — Oblon, McClelland, Maier & Neustadt, L.L.P.

(57) ABSTRACT

The length of the polycrystalline silicon rod (100) is measured with a tape measure, then the polycrystalline silicon rod (100) is hit with a hammer (120), and this hammering sound is recorded in a recorder (140) through a microphone (130). Then, an acoustic signal of the hammering sound is subjected to a fast Fourier transform and a frequency distribution is displayed. Furthermore, a peak frequency f is detected which shows the largest sound volume in the frequency distribution obtained after the fast Fourier transform. The relationship between the length (L) of the polycrystalline silicon rod and the peak frequency f is obtained, and the firmness of the polycrystalline silicon rod is determined on the basis of whether or not the peak frequency f is in a range of f≥1,471/L (region A).

20 Claims, 7 Drawing Sheets (51) Int. Cl.
*G01R 31/26* (2014.01)
*C01B 33/035* (2006.01)
*G01N 29/04* (2006.01)
*G01N 29/44* (2006.01)
*G01N 29/46* (2006.01)
*G01N 29/12* (2006.01)

(52) U.S. Cl.
CPC ........... *G01N 29/4454* (2013.01); *G01N 29/46* (2013.01); *G01N 2291/0234* (2013.01); *G01N 29/12* (2013.01); *G01N 2291/2626* (2013.01); *H01L 2924/0002* (2013.01); *H01L 2224/16* (2013.01)

(56) References Cited

FOREIGN PATENT DOCUMENTS

| | | |
|---|---|---|
| JP | 2001 294416 | 10/2001 |
| JP | 2002-340869 A | 11/2002 |
| JP | 2004 149324 | 5/2004 |
| JP | 2007 218638 | 8/2007 |
| JP | 2008 58314 | 3/2008 |

OTHER PUBLICATIONS

Guan-Hua Wu, et al., "Evolution of the acoustic impact testing method", NDT, Feb. 2011, pp. 35-41 (with English Abstract).
International Search Report Issued Sep. 20, 2011 in PCT/JP11/03800 Filed Jul. 4, 2011.

* cited by examiner

POLYCRYSTALLINE SILICON ROD AND METHOD FOR MANUFACTURING POLYCRYSTALLINE SILICON ROD

TECHNICAL FIELD

The present invention relates to a polycrystalline silicon rod and a method for manufacturing the polycrystalline silicon rod, and more specifically relates to a technology of simply sorting a firm polycrystalline silicon rod.

BACKGROUND ART

The Siemens method is known as a method for manufacturing polycrystalline silicon which becomes a raw material of single crystal silicon for use in manufacturing a semiconductor device or of silicon for use in manufacturing a solar cell. The Siemens method is a method of bringing a source gas containing chlorosilane into contact with a heated silicon core wire and thereby growing polycrystalline silicon on the surface of this silicon core wire in the vapor phase by using a CVD (Chemical Vapor Deposition) method.

When polycrystalline silicon is grown according to the Siemens method, silicon core wires are assembled into a guard frame shape consisting of the two wires in perpendicular directions and one wire in horizontal direction in a reactor of a vapor-phase growth apparatus, and both ends of the silicon core wire constituting this guard frame shape are fixed on a pair of metal electrodes which are arranged on a base plate through a pair of core wire holders.

Next, a source gas such as a mixture gas of trichlorosilane and hydrogen is supplied into the reactor through a gas nozzle, while the silicon core wire is heated in a temperature range of 900° C. or higher and 1,200° C. or lower in a hydrogen atmosphere by an electric conduction of an electric current passed from the metal electrode, then crystals of silicon grow on the silicon core wire, and polycrystalline silicon with a desired diameter is formed into an inverted U-shape.

When single crystal silicon is produced with an FZ (Floating Zone) method using polycrystalline silicon which has been grown in the vapor phase according to the Siemens method, polycrystalline silicon with the above described inverted U-shape is subjected to the treatments of: preparing a polycrystalline silicon rod with a desired length through a cutting process of cutting both ends of the polycrystalline silicon (cutting process); grinding the perimeter of this polycrystalline silicon rod so that the diameter becomes equal in a longitudinal direction and the surface becomes uniform (cylinder grinding process); further machining one end of this polycrystalline silicon rod to sharpen the end (tip machining process); and finally etching the surface of the polycrystalline silicon rod to remove impurities and distortion (etching process).

In such a polycrystalline silicon rod, cracking (crack) tends to be easily formed in inside and outside parts, in the vapor-phase growth process or a cooling stage after the growth, along with a large diameter tendency in recent years.

When the cracking is formed in the inside and outside parts of the polycrystalline silicon rod, the rod may be broken in the above described cutting process, cylinder grinding process, tip machining process, or etching process. Alternatively, in the worst case, the polycrystalline silicon rod may be cracked in a process of growing a single crystal silicon ingot with an FZ method. If the polycrystalline silicon rod is cracked in any of these processes, not only the process operation conducted before the time becomes useless, but also even the equipment which is used in the process may be damaged.

In addition, when the polycrystalline silicon rod is used as a supplemental charge material or a recharge material in the process of growing the single crystal silicon ingot with the CZ (Czochralski) method, if there is the cracking in the inside and outside parts of the polycrystalline silicon rod, the polycrystalline silicon rod may be ruptured initiating from the cracking while being machined so as to become usable in a rod shape as it is or while being lowered into a crucible in a CZ furnace heated to a high temperature, and may fall into the CZ furnace to scatter a silicon melt or destroy the crucible.

Here, the supplemental charge means to increase the amount of the melt in the crucible by making the polycrystalline silicon rod which has been hung above the crucible gradually melt into the melt, after a silicon lump which has been charged into the crucible has been melt. In addition, the recharge means to increase the amount of the melt in the crucible by making the polycrystalline silicon rod which has been hung above the crucible gradually melt into a remaining melt, after the CZ crystal has been pulled up.

Conventionally, various techniques are proposed in order to detect the cracking of the inside and outside parts of polycrystalline silicon. For instance, Japanese Patent Laid-Open No. 2001-21543 (Patent Literature 1) discloses a flaw detection method of placing a polycrystalline silicon lump in water or another liquid, transmitting and receiving a sound wave of 0.5 to 10 MHz while making a probe scan the polycrystalline silicon lump, in an upside of the polycrystalline silicon lump, and displaying an abnormal portion right under the probe on a two-dimensional plane.

In addition, Japanese Patent Laid-Open No. 2007-218638 (Patent Literature 2) discloses a crack inspection method of comparing image data provided by an infrared transmission light through a polycrystalline silicon wafer, with image data provided by an infrared reflection light therefrom, obtaining a difference between brightnesses or luminances of each pixel corresponding to the same position, and determining whether there is a crack in the inside and outside parts of the polycrystalline silicon wafer or not.

CITATION LIST

Patent Literature

Patent Literature 1: Japanese Patent Laid-Open No. 2001-21543

Patent Literature 2: Japanese Patent Laid-Open No. 2007-218638

SUMMARY OF INVENTION

Technical Problem

However, the flaw detection method and the crack inspection method disclosed in Patent Literature 1 and Patent Literature 2 need an inspection device essentially on a large scale. In addition, conventionally, a crack inspection has been conducted which is based on a hammering sound due to hammering by an operator, but this hammering sound inspection is a sensory inspection, and essentially causes variations of determination depending on each operator.

The present invention has been designed so as to solve such conventional cracking (crack) of polycrystalline silicon, and an object of the present invention is to provide a technique for sorting a polycrystalline silicon rod which is firm and crack-resistant, with high accuracy and without needing a device on a large scale, and eventually to provide a polycrystalline silicon rod of high quality.

Solution to Problem

In order to solve the above described problems, the method for manufacturing the polycrystalline silicon rod of the present invention includes: growing polycrystalline silicon with a vapor phase method; forming the polycrystalline silicon into a polycrystalline silicon rod having a length of L (m); analyzing the frequency of a hammering sound obtained by hitting the polycrystalline silicon rod; determining a peak frequency f (Hz) of the hammering sound; and sorting a polycrystalline silicon rod which satisfies f≥1,471/L.

An upper limit of the frequency f may be specified to satisfy f≤1,471/L+1,000, as a sorting standard for the polycrystalline silicon rod.

Alternatively, it may be specified that the above described polycrystalline silicon rod to be sorted out has such a ratio R ($f_0/f$) of a natural frequency $f_0$ obtained from the waveform of the hammering sound to the above described peak frequency f as to satisfy 0.9≤R≤1.1.

The polycrystalline silicon rod of the present invention is a polycrystalline silicon rod that has a length of L (m), wherein a hammering sound of the polycrystalline silicon rod has such a peak frequency f (Hz) as to satisfy f≥1,471/L, which is obtained by analyzing the frequency of the sound.

It may also be specified that the peak frequency f satisfies f≤1,471/L+1,000.

Alternatively, it may be specified that a ratio R ($f_0/f$) of a natural frequency $f_0$ obtained from a waveform of the hammering sound of the above described polycrystalline silicon rod to the above described peak frequency f satisfies 0.9≤R≤1.1.

The polycrystalline silicon rod is obtained, for instance, with a vapor-phase growth process according to a Siemens method.

Advantageous Effects of Invention

The method according to the present invention can be carried out if there are, for instance, a hammer for hitting the polycrystalline silicon rod, a voice recorder for recording the hammering sound, a software and a PC (personal computer) for use in frequency analysis, and a tape measure for measuring the length of the polycrystalline silicon rod, and accordingly can be easily conducted without needing a device on a large scale.

The method according to the present invention sorts a polycrystalline silicon rod which is firm and crack-resistant, and thereby a polycrystalline silicon rod of high quality can be manufactured.

In addition, the method can uniquely determine the presence or absence of cracking in the inside and outside parts of the polycrystalline silicon rod, and accordingly does not cause such variations as to occur in a sensory inspection or the like.

DESCRIPTION OF EMBODIMENTS

An embodiment for carrying out the present invention will be described below with reference to the drawings.

Figure 1:
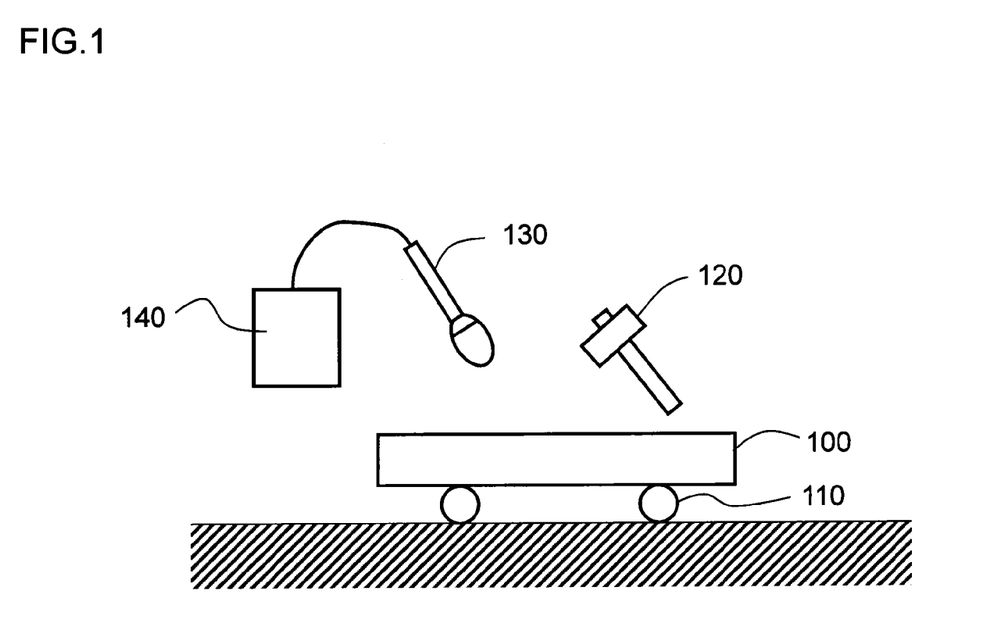
FIG. 1 is a schematic view for describing one embodiment of a method for sorting a polycrystalline silicon rod in the present invention.

FIG. 1 is a schematic view for describing one embodiment of a method for sorting a polycrystalline silicon rod in the present invention. In the figure, reference numeral 100 denotes a polycrystalline silicon rod to be sorted. The polycrystalline silicon rod 100 illustrated here is obtained with the above described vapor-phase growth process according to the Siemens method, and has a diameter of approximately 110 mm and a length of approximately 1,600 mm. In addition, reference numeral 110 denotes a roller for mounting the polycrystalline silicon rod 100 thereon, reference numeral 120 denotes a hammer for hitting the polycrystalline silicon rod 100, reference numeral 130 denotes a microphone for picking up a sound which is generated by hitting with the hammer 120 and is emitted from the polycrystalline silicon rod 100, and reference numeral 140 denotes a recorder for recording the hammering sound which has been picked up by the microphone 130.

The sorting method of the present invention includes: hitting the polycrystalline silicon rod 100 with the hammer 120; analyzing the frequency of the hammering sound generated by hitting with the hammer 120; and determining the firmness of the polycrystalline silicon rod 100. For this reason, it is desirable for obtaining an original hammering sound of the polycrystalline silicon rod 100 that the polycrystalline silicon rod 100 does not come in contact with other members as much as possible. In other words, it is desirable for accurately analyzing the frequency to hold the polycrystalline silicon rod 100 in such a state that an area contacting another member is as small as possible. For this reason, in the example illustrated in FIG. 1, the polycrystalline silicon rod 100 is mounted on the two rollers 110.

The hammer 120 for use in hitting the polycrystalline silicon rod 100 is desirably formed from a material which does not almost contaminate the polycrystalline silicon rod 100 with a heavy metal when the rod has been hit. For instance, it is desirable to use a plastic hammer or a tungsten hammer.

When the polycrystalline silicon rod 100 is hit with the hammer 120, a hammering sound of 100 Hz to 5,000 Hz is generated. As the polycrystalline silicon rod 100 becomes longer, the frequency of the hammering sound becomes lower. In addition, when the polycrystalline silicon rod 100 has cracking formed in the inside and outside parts thereof, the frequency of the hammering sound becomes lower.

The hammering sound emitted from the polycrystalline silicon rod 100 is picked up by the microphone 130, and is recorded in the recorder 140. When a digital voice recorder is used as the recorder 140, for instance, the acoustic signal is converted from analog to digital and the digital signal is recorded.

Figure 2:
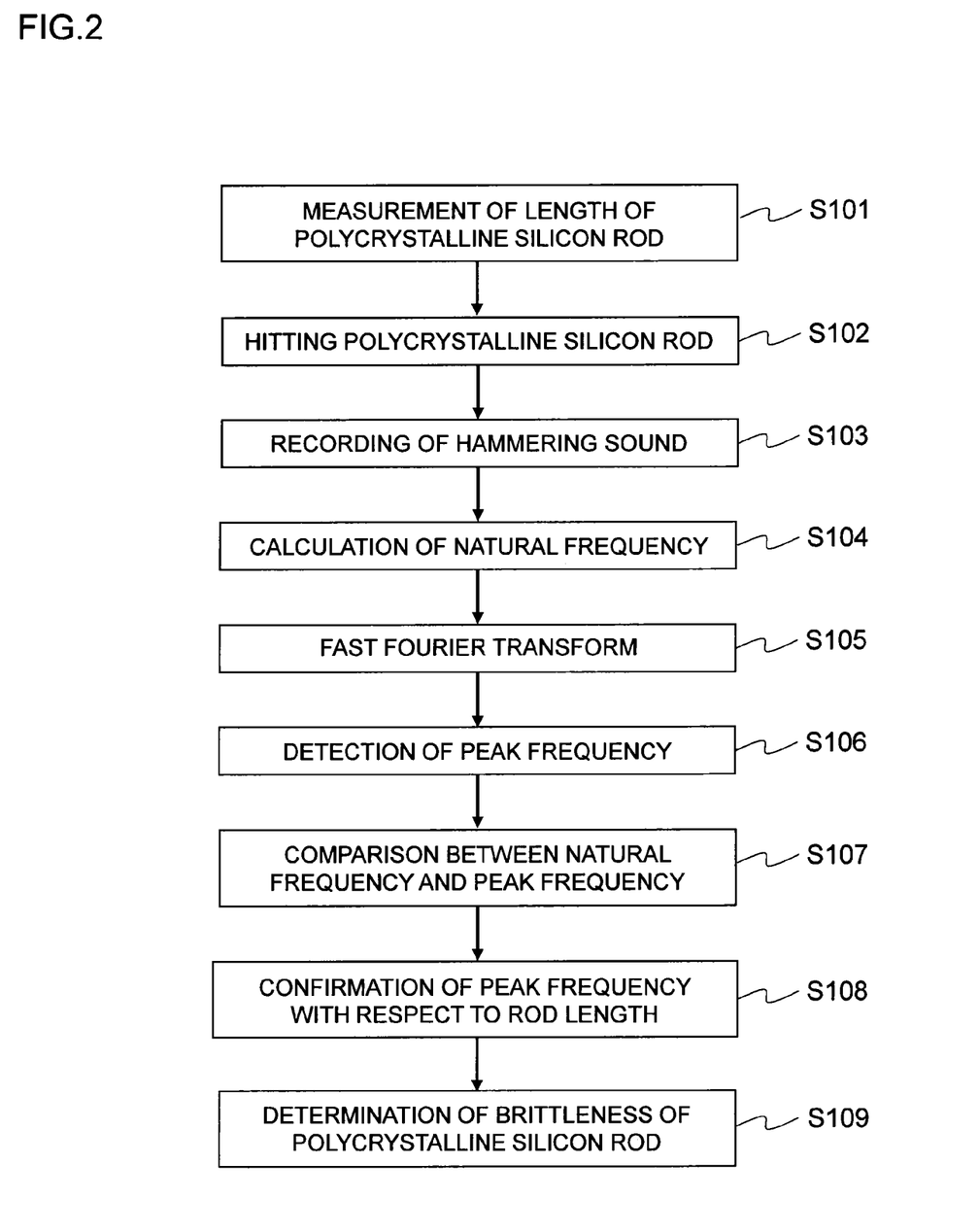
FIG. 2 is a flow chart for describing a procedure of analyzing a frequency of a hammering sound emitted from the polycrystalline silicon rod in the present invention.

FIG. 2 is a flow chart for describing a procedure of analyzing a frequency of a hammering sound emitted from the polycrystalline silicon rod, in the present invention. Firstly, the length of the polycrystalline silicon rod 100 is measured with a tape measure (S101). Next, the polycrystalline silicon rod 100 is hit with the hammer 120 (S102); and this hammering sound is recorded in the recorder 140 through the microphone 130 (S103). Then, this hammering sound is analyzed and a natural frequency $f_0$ is calculated (S104); the acoustic signal of the hammering sound is subjected to a fast Fourier transform (Fast Fourier Transform: FFT); and the frequency distribution is displayed (S105).

Figure 3A:
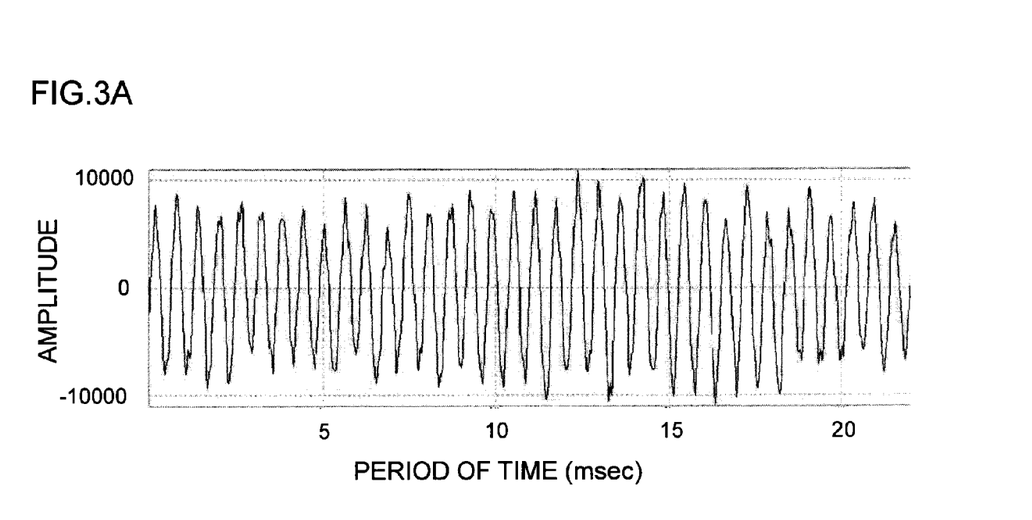
FIG. 3A is a view illustrating one example of an acoustic signal of the hammering sound.
Figure 3B:
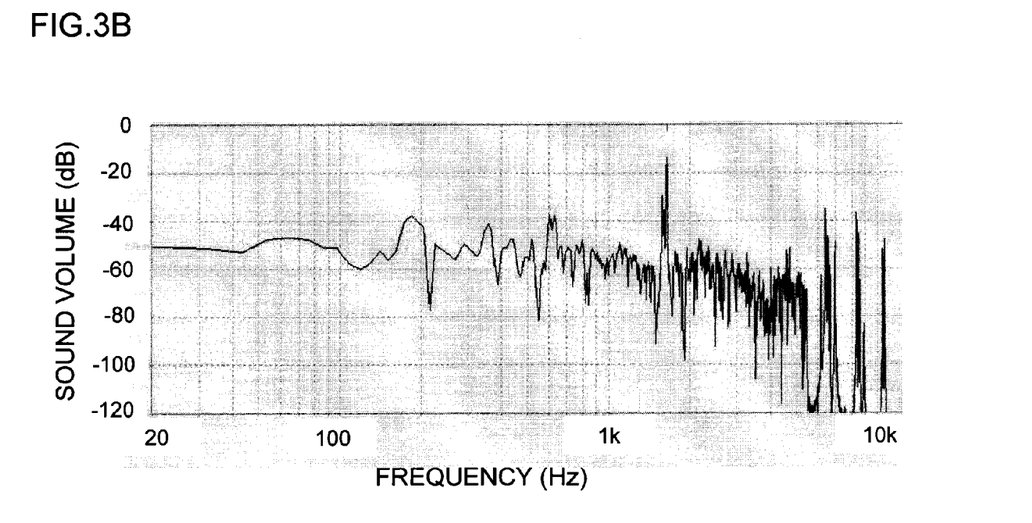
FIG. 3B is a view illustrating one example of a frequency distribution obtained by subjecting the acoustic signal of the hammering sound to a fast Fourier transform.

FIG. 3A and FIG. 3B are one example of the acoustic signal of the hammering sound, and one example of a frequency distribution obtained by subjecting the acoustic signal to the fast Fourier transform, respectively.

Firstly, a period of time between a crest and a next crest (or trough and next trough) in the acoustic signal waveform of the hammering sound illustrated in FIG. 3A is read, in other words, a time cycle is read, and the inverse number of the value is obtained as a natural frequency $f_0$. Subsequently, as is illustrated in FIG. 3B, the frequency distribution is obtained by subjecting the acoustic signal to the fast Fourier transform. For information, a free software in which the acoustic signal that has been converted to digital is subjected to the fast Fourier transform is available on the Internet.

The waveform of the hammering sound generated when a portion having no cracking in the polycrystalline silicon rod 100 is hit with the hammer 120 is close to a sinusoidal wave, and the frequency showing a large sound volume is one or two, which is observed in the frequency distribution after the fast Fourier transform.

In contrast to this, when a portion having cracking in the polycrystalline silicon rod 100 is hit with the hammer 120, the generated hammering sound is similar to a sound which would be generated if a plurality of polycrystalline silicon rods having different lengths little by little have been hit at a time. Specifically, a large number of sound waves having slightly different frequencies are formed, and the waveform of the hammering sound becomes a waveform similar to that of a beat, in one time cycle of which there are a large number of crests and troughs. Because of this, the time cycle of the waveform becomes long, the frequency becomes low, and the hammering sound becomes heard in a low tone. If the acoustic signal of such a hammering sound has been subjected to the fast Fourier transform, the obtained frequency distribution shows a large number of frequencies having a comparatively large sound volume.

Then, in the present invention, a peak frequency f is detected which shows the largest sound volume in the frequency distribution obtained after the fast Fourier transform (S106). This peak frequency f is a main frequency which forms the hammering sound, and if the waveform of the hammering sound has been formed by a single sinusoidal wave, the peak frequency f coincides completely with the natural frequency $f_0$. On the other hand, when the waveform of the hammering sound is formed by the large number of the sound waves which are superimposed on others, the peak frequency f becomes deviated from the natural frequency $f_0$.

Then, the natural frequency $f_0$ and the peak frequency f are compared (S107).

When the number of the sound waves which form the waveform of the hammering sound is comparatively small and a difference between frequencies of the sound waves is small, the waveform of the hammering sound stays on such a degree that the time cycle of a sinusoidal wave becomes slightly long, and accordingly the natural frequency $f_0$ becomes slightly smaller than the peak frequency f.

In contrast to this, when the number of the sound waves which form the waveform of the hammering sound becomes large, and the waveform of the beat becomes clearly recognized, the frequency of the beat becomes the peak frequency f. At this time, the time cycle of the beat is longer than the time cycle of the hammering sound, and accordingly the natural frequency $f_0$ becomes larger than the peak frequency f.

According to the investigation by the present inventors, as a result of having measured the natural frequency $f_0$ and the peak frequency f of 31 polycrystalline silicon rods in total, and examined a relationship between the frequencies and cracking, there were 10 polycrystalline silicon rods having the cracking, and 21 polycrystalline silicon rods having no cracking. In addition, a value (R) was determined for each of these polycrystalline silicon rods, by dividing the natural frequency $f_0$ by the peak frequency f, and the value was consequently 0 or more and 2 or less.

Next, the upper limit value of the value (R) obtained by dividing the natural frequency $f_0$ by the peak frequency f was gradually lowered and the lower limit value was gradually raised to limit the range between the values gradually, and the number of the polycrystalline silicon rods having the cracking and the number of the polycrystalline silicon rods having no cracking were examined, which belonged within the limited range. The result is shown in Table 1.

TABLE 1

| R | Cracking present | No cracking | Total |
|---|---|---|---|
| $0 \leq R \leq 2$ | 10 rods | 21 rods | 31 rods |
| $0.1 \leq R \leq 1.9$ | 9 rods | 21 rods | 30 rods |
| $0.2 \leq R \leq 1.8$ | 9 rods | 21 rods | 30 rods |
| $0.3 \leq R \leq 1.7$ | 9 rods | 21 rods | 30 rods |
| $0.4 \leq R \leq 1.6$ | 8 rods | 21 rods | 29 rods |
| $0.5 \leq R \leq 1.5$ | 7 rods | 21 rods | 28 rods |
| $0.6 \leq R \leq 1.4$ | 7 rods | 21 rods | 28 rods |
| $0.7 \leq R \leq 1.3$ | 6 rods | 21 rods | 27 rods |
| $0.8 \leq R \leq 1.2$ | 5 rods | 20 rods | 25 rods |
| $0.9 \leq R \leq 1.1$ | 1 rod | 19 rods | 20 rods |
| $0.95 \leq R \leq 1.05$ | 0 rod | 11 rods | 11 rods |

As is illustrated in Table 1, when the value (R) obtained by dividing the natural frequency $f_0$ by the peak frequency f was limited to 0.5 or more and 1.5 or less, 7 polycrystalline silicon rods out of 10 polycrystalline silicon rods having the cracking, in other words, 70% of polycrystalline silicon rods having the cracking could not be distinguished from the polycrystalline silicon rods having no cracking. However, when the range of the R-value is limited to 0.9 or more and 1.1 or less, the number of the polycrystalline silicon rods having the cracking was slightly only one, which could not be distinguished from the polycrystalline silicon rods having no cracking.

When the range of the R-value is limited to 0.9 or more and 1.1 or less, there are 19 polycrystalline silicon rods having no cracking in this R-value range, which are smaller than the whole number (21 rods) by only 2 polycrystalline silicon rods. In other words, it is understood that the R-value of the most of the polycrystalline silicon rods having no cracking is in a range of 0.9 or more and 1.1 or less. In contrast to this, the number of the polycrystalline silicon rods is only one, which have the cracking and are in the R-value in a range of 0.9 or more and 1.1 or less. The R-values of the most of the polycrystalline silicon rods having the cracking are either less than 0.9 or more than 1.1.

Figure 4:
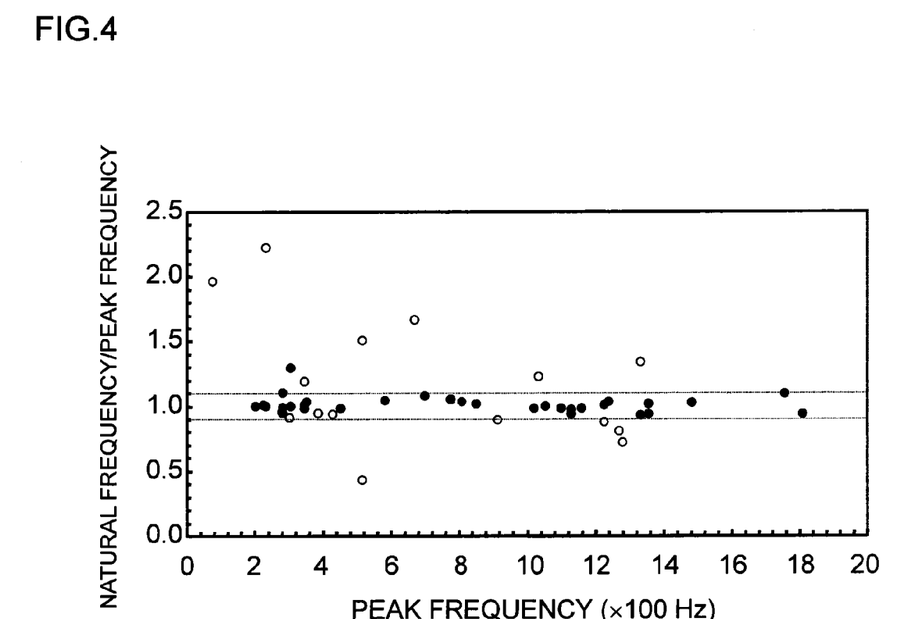
FIG. 4 is a view illustrating a result of having obtained a relationship between a value obtained by dividing a natural frequency by a peak frequency and the peak frequency of the polycrystalline silicon rod.

FIG. 4 is a view illustrating a result of having obtained a relationship between the above described R-value and the peak frequency f, on another population of polycrystalline silicon rods than that illustrated in Table 1 collectively. Incidentally, a black dot represents a value of the polycrystalline silicon rod having no cracking, and a white dot represents a value of the polycrystalline silicon rod having the cracking.

As is illustrated in FIG. 4, the most of the polycrystalline silicon rods (white dot) having the cracking show the R-value of less than 0.9 or more than 1.1, but some of them show the R-value in a range of 0.9 or more and 1.1 or less.

Figure 5:
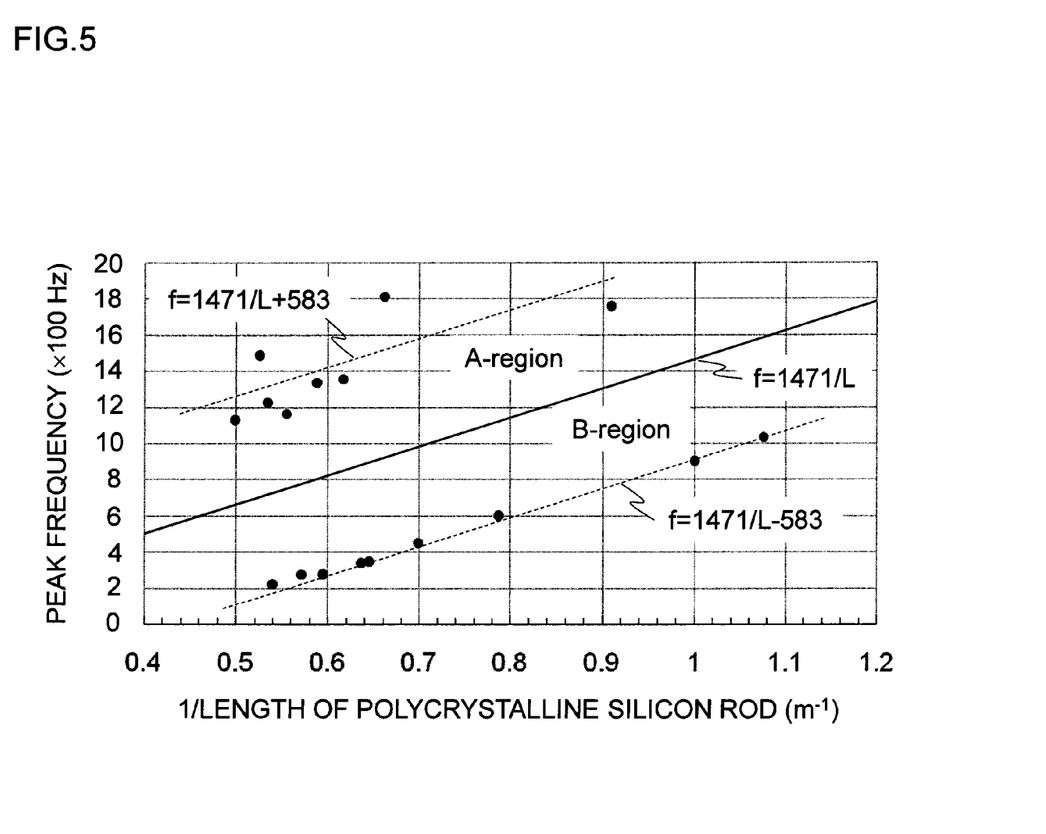
FIG. 5 is a graph illustrating a relationship between the length and the peak frequency of the polycrystalline silicon rod having an R-value of 0.9 or more and 1.1 or less.

FIG. 5 is a graph illustrating a relationship between the length (L) and the peak frequency of the polycrystalline silicon rods of which the R-values are 0.9 or more and 1.1 or less. A horizontal axis represents an inverse number (unit $m^{-1}$) of the length (L) of the polycrystalline silicon rod, and a vertical axis represents the peak frequency thereof (f: unit Hz).

From the result illustrated in FIG. 5, such a tendency can be clearly read that the polycrystalline silicon rods are classified into any of a region having a comparatively high peak frequency (region A) and a region having a comparatively low peak frequency (region B), even though showing approximately the same R-value. In addition, such a tendency is recognized that as the polycrystalline silicon rod becomes longer, in other words, as the value of the horizontal axis is smaller, the peak frequency (f) becomes lower, in any region.

The peak frequencies of the polycrystalline silicon rods belonging to the above described region A have mostly a relationship of f=1,471/L+583. In addition, the peak frequencies of the polycrystalline silicon rods belonging to the region B have mostly a relationship of f=1,471/L−583. Accordingly, when a boundary between the region A and the region B is defined as a middle between the above described two relational expressions, the boundary line becomes f=1,471/L.

In other words, the peak frequencies of the polycrystalline silicon rods belonging to the region A result in satisfying f≥1,471/L. However, according to an investigation result by the present inventors, the peak frequencies of the polycrystalline silicon rods belonging to the region A are in a range of f≤1,471/L+1,000.

As is illustrated in FIG. 5, the peak frequencies of the polycrystalline silicon rods belonging to the region B are comparatively lower than the peak frequencies of the polycrystalline silicon rods belonging to the region A, and the polycrystalline silicon rods belonging to the region B can be comparatively easily cracked when having been hit with a hammer. In contrast to this, the polycrystalline silicon rods belonging to the region A are firm, and are crack-resistant even if having been hit with the hammer. In other words, it can be determined whether the polycrystalline silicon rod is firm and crack-resistant or not, by analyzing the frequency of a hammering sound, by knowing which region out of the above described region A or region B the peak frequency f belongs to.

Then, in the present invention, on the basis of the above described principle, the peak frequency with respect to the length of the polycrystalline silicon rod is confirmed (S108); and it is determined how firm the polycrystalline silicon rod is and consequently whether the polycrystalline silicon rod is crack-resistant or not (S109).

Figure 6:
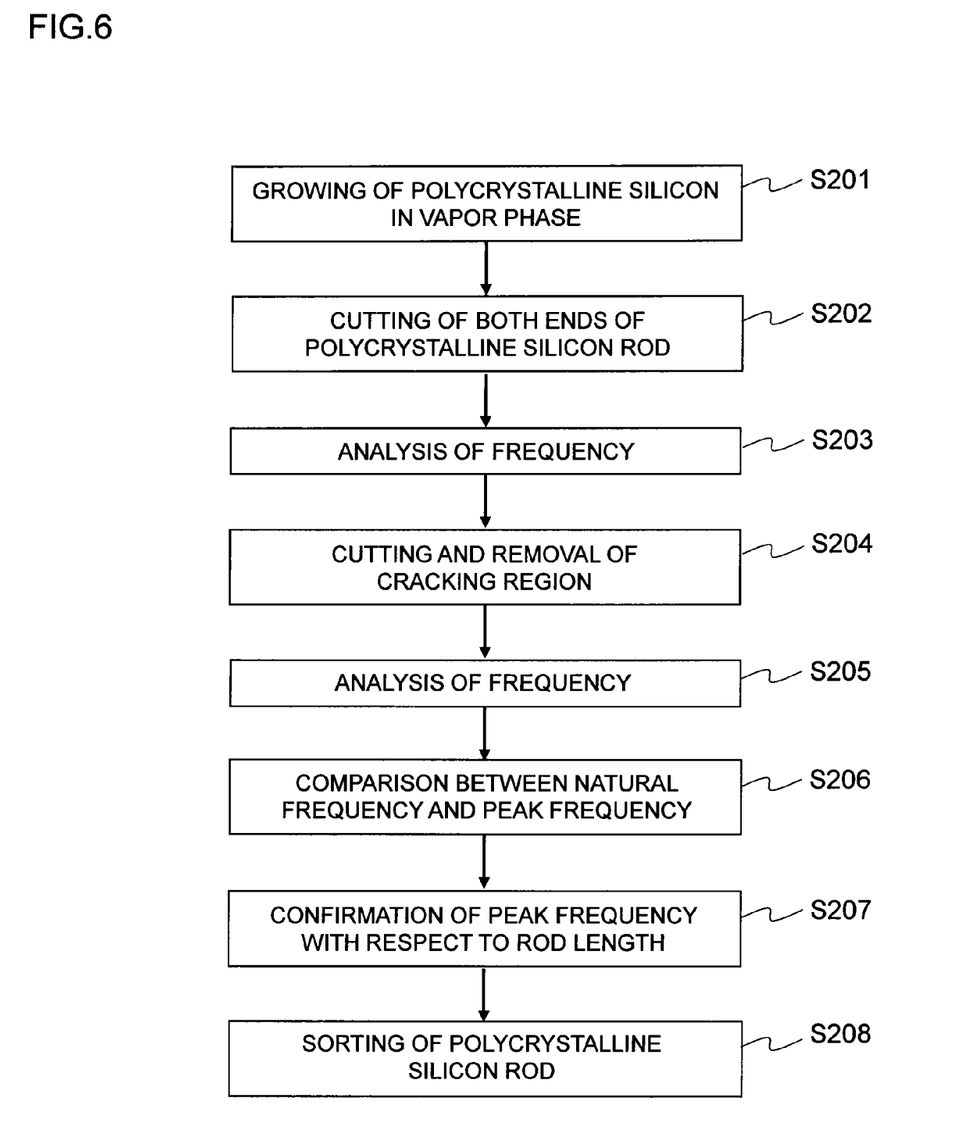
FIG. 6 is a flow chart illustrating an example of a process for sorting the polycrystalline silicon rod having no cracking formed in the inside and outside parts thereof.
Figure 7:
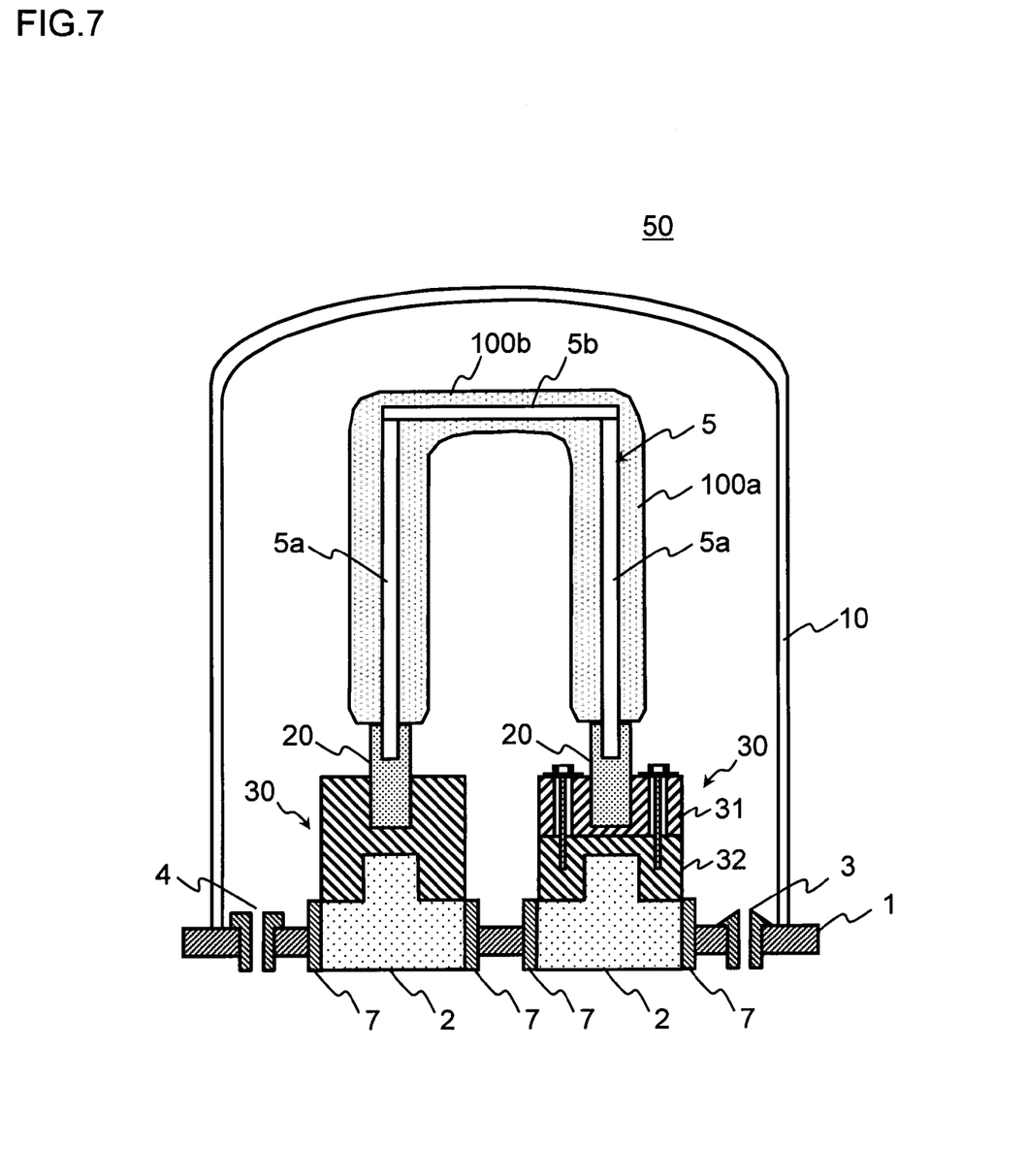
FIG. 7 is a schematic view illustrating an example of a structure of an apparatus for use in the manufacture of the polycrystalline silicon rod.

FIG. 6 is a flow chart illustrating an example of a process for sorting a firm polycrystalline silicon rod. FIG. 7 is a schematic view illustrating an example of a structure of an apparatus for use in the manufacture of the polycrystalline silicon rod.

With reference to FIG. 7, the apparatus 50 for manufacturing polycrystalline silicon is an apparatus for growing polycrystalline silicon on the surface of a silicon core wire in the vapor phase according to a Siemens method, and has a structure roughly including a base plate 1 and a reaction vessel 10. The polycrystalline silicon 100 to be obtained includes a straight body portion 100a which grows on a vertical portion 5a of a silicon core wire 5 that has been assembled into a guard frame shape in the vapor phase, and a bridge portion 100b which grows on a horizontal portion (bridge portion 5b) in the vapor phase.

The base plate 1 has a metal electrode 2 for supplying an electric current to the silicon core wire 5 therethrough, a gas nozzle 3 for supplying a process gas therethrough such as nitrogen gas, hydrogen gas and trichlorosilane gas, and an exhaust port 4 for discharging an exhaust gas therethrough arranged therein.

The metal electrode 2 is connected to another not-shown metal electrode or a power source arranged in the outside of the reactor, and receives an electric power from the outside. This metal electrode 2 has insulators 7 provided on its side faces, and passes through the base plate 1 in a state of being sandwiched by these insulators 7.

As is illustrated in FIG. 7, when the polycrystalline silicon 100 is grown in a vapor phase, two core wires (5a) in a vertical direction and one core wire (5b) in a horizontal direction are assembled in the reactor 10 to form the silicon core wire 5 with the guard frame shape; both end portions of the portions 5a in the vertical direction of the silicon core wire 5 are fixed by core wire holders 20 which are held in carbon electrodes 30, respectively; and an external electric power which has been supplied to the metal electrodes 2 is passed to the silicon core wire 5 through the carbon electrodes 30.

Incidentally, the metal electrode 2, the base plate 1 and the reactor 10 are cooled by using a cooling medium. In addition, both of the core wire holder 20 and the carbon electrode 30 are formed of graphite.

Firstly, polycrystalline silicon with an inverted U-shape is grown in a vapor phase in the apparatus having a structure illustrated in FIG. 7 according to the Siemens method (S201).

After the growth of the polycrystalline silicon in the vapor phase has been finished, the polycrystalline silicon with the inverted U-shape is taken out from the reactor 10, and is divided into the straight body portion 100a and the bridge portion 100b. However, the cracking remains in both ends of the polycrystalline silicon rod 100 in many cases, and accordingly both ends of the polycrystalline silicon rod 100 are cut (S202).

Next, as is illustrated in FIG. 1, the polycrystalline silicon rod 100 is mounted on rollers 110 and is hit with a hammer 120, and a hammering sound is recorded through a microphone 130. Then, the frequency of the above described hammering sound is analyzed in the procedure which has been described with reference to FIG. 2, and it is confirmed whether the value obtained by dividing the natural frequency $f_0$ by the peak frequency f is 0.9 or more and 1.1 or less (S203) in all regions, or not.

For information, instead of hitting the whole polycrystalline silicon rod 100 with the hammer 120, recording only a hammering sound in a region in which the sound is comparatively low and analyzing the frequency of the hammering sound may be adopted as a simple method.

When there is a region in which the value obtained by dividing the natural frequency $f_0$ by the peak frequency f is less than 0.9 or more than 1.1, it is considered that cracking exists in the inside or outside parts, and accordingly the region is cut and removed (S204). Incidentally, in this case, the frequency is analyzed again after the cracking region has been cut and removed (S205). In addition, the steps S204 and S205 are repeated a plurality of times, as needed, and it is confirmed finally that the value obtained by dividing the natural frequency $f_0$ by the peak frequency f is 0.9 or more and 1.1 or less in all regions (S206).

Next, the length L of the polycrystalline silicon rod 100 is measured with a tape measure or the like, and it is confirmed whether the above described peak frequency belongs to the above described region A or region B with respect to the inverse number 1/L of the length L of the polycrystalline silicon rod 100 (S207). The polycrystalline silicon rod 100 belonging to the region A is firmer and more crack-resistant than that belonging to the region B. In other words, the polycrystalline silicon rod which is firm and crack-resistant can be obtained, by sorting the polycrystalline silicon rod of which the hammering sound belongs to the region A from the polycrystalline silicon rod of which the hammering sound belongs to the region B (S208).

EXAMPLE 1

Both ends of the polycrystalline silicon which was obtained by growing the polycrystalline silicon in a vapor phase according to a Siemens method were cut, and a polycrystalline silicon rod 100 with a length of 1.2 m and a diameter of 121 mm was prepared. This polycrystalline silicon rod 100 was hit with a hammer 120 made from tungsten carbide, and the hammering sound was recorded in a digital voice recorder 140 provided with a microphone 130. The natural frequency of the recorded hammering sound was 1,563 Hz.

Subsequently, the acoustic signal of this hammering sound was subjected to a fast Fourier transform and frequency distribution was displayed. As a result, the peak frequency was 1,636.5 Hz. At this time, a value obtained by dividing the natural frequency by the peak frequency is 0.96. In addition, when the length of 1.2 m of the polycrystalline silicon rod is substituted into the expression (f=1,471/L) which expresses the boundary line between the above described region A and region B, the peak frequency on the boundary becomes approximately 1,226 Hz (=1,471/1.2), but the above described peak frequency (1,636.5 Hz) is higher than this peak frequency on the boundary. Accordingly, the polycrystalline silicon rod 100 was sorted as the rod belonging to the region A.

As a result of having visually inspected this polycrystalline silicon rod 100 under a fluorescent lamp, no cracking was observed. Furthermore, both ends of the polycrystalline silicon rod 100 were cut, the cylinder thereof was polished, the tip thereof was machined, and the polycrystalline silicon rod was etched, and a monocrystal ingot was grown with an FZ method, but in a series of these processes, the polycrystalline silicon rod 100 did not cause the cracks therein.

COMPARATIVE EXAMPLE 1

A polycrystalline silicon rod with a length of 1.5 m and a diameter of 122 mm was obtained with a Siemens method, and the natural frequency and the peak frequency were measured, in a similar way to that in the above described Example 1. As a result, the natural frequency was 147 Hz, the peak frequency was 75.4 Hz, and the value obtained by dividing the natural frequency by the peak frequency was 1.96.

When the length of 1.5 m of the polycrystalline silicon rod is substituted into the expression (f=1,471/L) which expresses the boundary line between the above described region A and region B, the peak frequency on the boundary becomes approximately 981 Hz (=1,471/1.5), but the above described peak frequency (75.4 Hz) is much lower than this peak frequency on the boundary. Accordingly, the polycrystalline silicon rod was sorted as the rod belonging to the region B.

In addition, as a result of having visually inspected this polycrystalline silicon rod under a fluorescent lamp, much cracking was observed, and the polycrystalline silicon rod was not machined as the polycrystalline silicon rod for use in growing FZ silicon ingot.

Thus, the present invention enables the firmness of a polycrystalline silicon rod and consequently the degree of crack resistance to be easily detected, enables a polycrystalline silicon rod which is crack-resistant to be sorted on the basis of this technique, and enables the polycrystalline silicon rod of high quality to be manufactured.

Industrial Applicability

According to the present invention, it is enabled to sort only a polycrystalline silicon rod which is firm and is crack-resistant, and it can be suppressed that the polycrystalline silicon rod for use in growing monocrystalline silicon with an FZ method or a CZ method causes cracks in the process.

REFERENCE SIGNS LIST

1 Base plate
2 Metal electrode
3 Gas nozzle
4 Exhaust port
5 Silicon core wire
5a Portion in vertical direction
5b Bridge portion
10 Reaction vessel
20 Core wire holder
30 Carbon electrode
31 Upper electrode
32 Lower electrode
50 Apparatus for manufacturing polycrystalline silicon
100 Polycrystalline silicon rod
110 Roller
120 Hammer
130 Microphone
140 Recorder

The invention claimed is:

1. A method for manufacturing a polycrystalline silicon rod, the method comprising:
   growing polycrystalline silicon with a vapor phase method;
   forming the polycrystalline silicon into a polycrystalline silicon rod having a length of L (m);
   hitting the polycrystalline silicon rod;
   analyzing a frequency of a hammering sound obtained by hitting the polycrystalline silicon rod;
   determining a peak frequency f (Hz) of the hammering sound; and
   sorting a polycrystalline silicon rod which satisfies f≥1,471/L.

2. The method of claim 1, wherein an upper limit of the peak frequency f is specified to satisfy f≤1,471/L+1,000, as a sorting standard for the polycrystalline silicon rod.

3. The method of claim 1, wherein the polycrystalline silicon rod to be sorted out has a ratio R ($f_0$/f) of a natural frequency $f_0$ obtained from a waveform of the hammering sound to the peak frequency f such that 0.9≤R≤1.1.

4. The method of claim 1, wherein the vapor phase method is a Siemens method.

5. The method of claim 2, wherein the polycrystalline silicon rod to be sorted has a ratio R ($f_0/f$) of a natural frequency $f_0$ obtained from a waveform of the hammering sound to the peak frequency f such that $0.9 \leq R \leq 1.1$.

6. The method of claim 2, wherein the vapor phase method is a Siemens method.

7. The method of claim 1, comprising hitting the polycrystalline silicon rod with a plastic hammer.

8. The method of claim 2, comprising hitting the polycrystalline silicon rod with a plastic hammer.

9. The method of claim 3, comprising hitting the polycrystalline silicon rod with a plastic hammer.

10. The method of claim 5, comprising hitting the polycrystalline silicon rod with a plastic hammer.

11. The method of claim 1, comprising hitting the polycrystalline silicon rod with a hammer comprising tungsten.

12. The method of claim 2, comprising hitting the polycrystalline silicon rod with a hammer comprising tungsten.

13. The method of claim 3, comprising hitting the polycrystalline silicon rod with a hammer comprising tungsten.

14. The method of claim 5, comprising hitting the polycrystalline silicon rod with a hammer comprising tungsten.

15. The method of claim 1, comprising hitting the polycrystalline silicon rod with a hammer comprising tungsten carbide.

16. The method of claim 2, comprising hitting the polycrystalline silicon rod with a hammer comprising tungsten carbide.

17. The method of claim 3, comprising hitting the polycrystalline silicon rod with a hammer comprising tungsten carbide.

18. The method of claim 5, comprising hitting the polycrystalline silicon rod with a hammer comprising tungsten carbide.

19. The method of claim 1, wherein the polycrystalline silicon rod is hit while mounted on two rollers.

20. The method of claim 2, wherein the polycrystalline silicon rod is hit while mounted on two rollers.

\* \* \* \* \*